(12) United States Patent
Bogert et al.

(10) Patent No.: US 12,644,786 B1
(45) Date of Patent: Jun. 2, 2026

(54) SYSTEMS AND METHODS FOR A SUTURE TENSIONOMETER DEVICE

(71) Applicant: Dignity Health, San Francisco, CA (US)

(72) Inventors: James Bogert, San Francisco, CA (US); James Mankin, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 308 days.

(21) Appl. No.: 18/328,527

(22) Filed: Jun. 2, 2023

Related U.S. Application Data

(60) Provisional application No. 63/348,053, filed on Jun. 2, 2022.

(51) Int. Cl.
*A61B 17/062* (2006.01)
*G01L 5/04* (2006.01)

(52) U.S. Cl.
CPC ............ *G01L 5/047* (2013.01); *A61B 17/062* (2013.01)

(58) Field of Classification Search
CPC .............. A61B 17/062; A61B 17/0625; A61B 2017/0488; A61B 2017/320044; A61B 17/285; A61B 17/295; A61B 17/29; A61B 17/30
See application file for complete search history.

(56) References Cited

U.S. PATENT DOCUMENTS

| | | | |
|---|---|---|---|
| 2005/0131390 A1* | 6/2005 | Heinrich .......... | A61B 17/07207 606/1 |
| 2011/0137337 A1* | 6/2011 | van den Dool ........ | A61B 17/29 606/205 |
| 2022/0265372 A1* | 8/2022 | Hufford ............... | A61B 90/361 |

\* cited by examiner

*Primary Examiner* — Darwin P Erezo
*Assistant Examiner* — Raihan R Khandker
(74) *Attorney, Agent, or Firm* — Polsinelli PC

(57) ABSTRACT

Various embodiments of a suture tensionometer for measuring a tensile force applied to a surgical suture are disclosed herein.

13 Claims, 13 Drawing Sheets

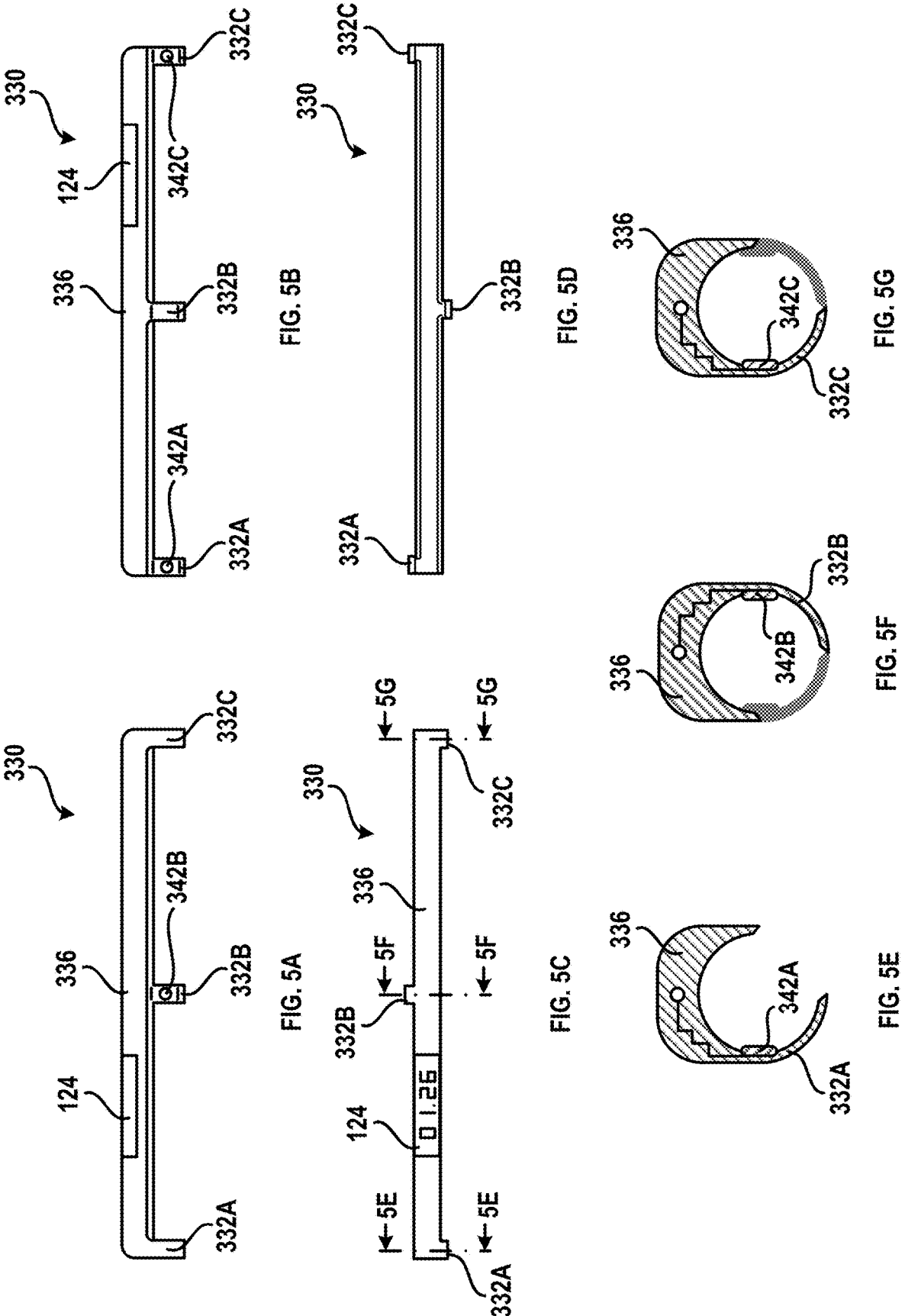

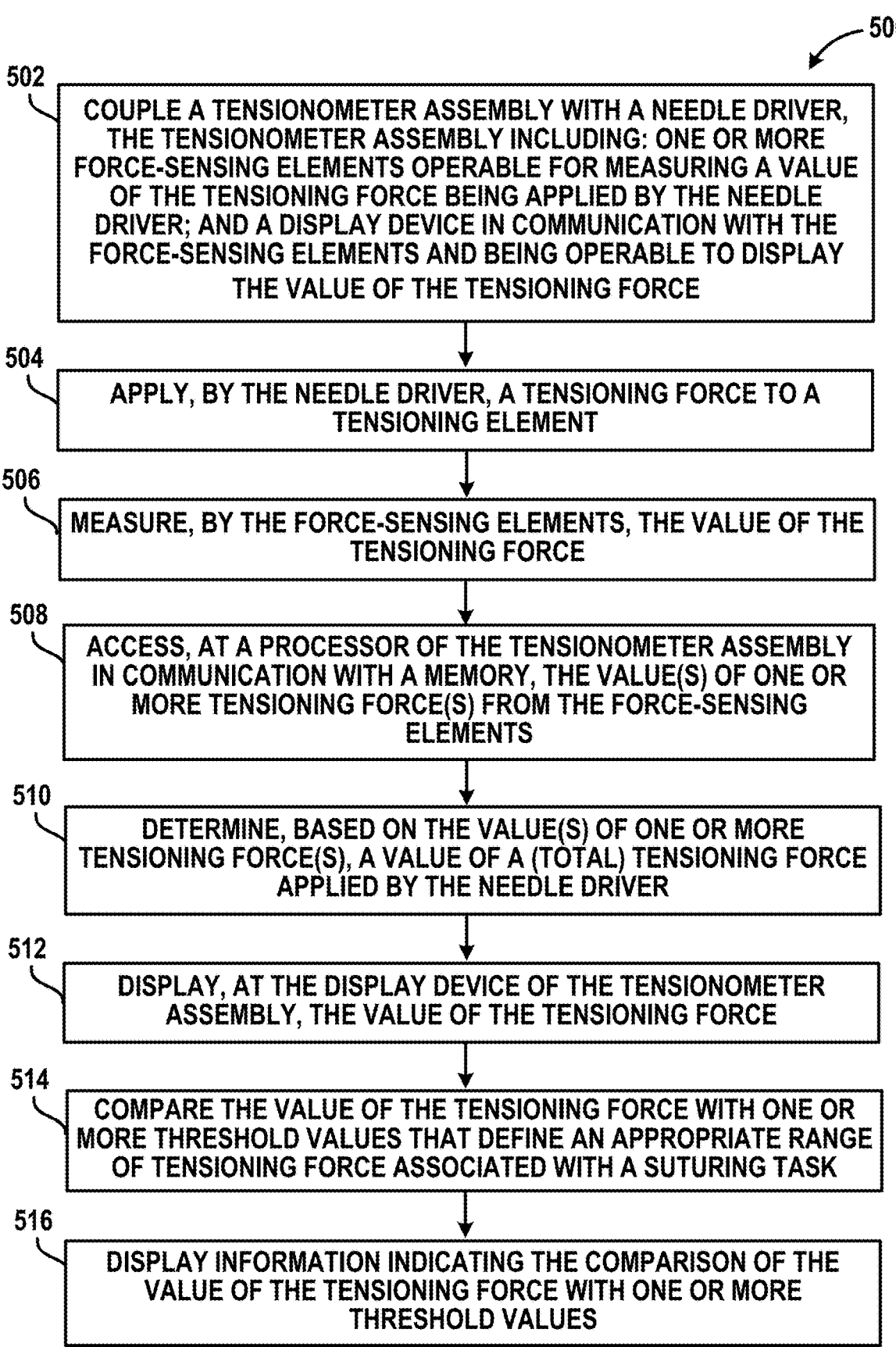

502 — COUPLE A TENSIONOMETER ASSEMBLY WITH A NEEDLE DRIVER, THE TENSIONOMETER ASSEMBLY INCLUDING: ONE OR MORE FORCE-SENSING ELEMENTS OPERABLE FOR MEASURING A VALUE OF THE TENSIONING FORCE BEING APPLIED BY THE NEEDLE DRIVER; AND A DISPLAY DEVICE IN COMMUNICATION WITH THE FORCE-SENSING ELEMENTS AND BEING OPERABLE TO DISPLAY THE VALUE OF THE TENSIONING FORCE

504 — APPLY, BY THE NEEDLE DRIVER, A TENSIONING FORCE TO A TENSIONING ELEMENT

506 — MEASURE, BY THE FORCE-SENSING ELEMENTS, THE VALUE OF THE TENSIONING FORCE

508 — ACCESS, AT A PROCESSOR OF THE TENSIONOMETER ASSEMBLY IN COMMUNICATION WITH A MEMORY, THE VALUE(S) OF ONE OR MORE TENSIONING FORCE(S) FROM THE FORCE-SENSING ELEMENTS

510 — DETERMINE, BASED ON THE VALUE(S) OF ONE OR MORE TENSIONING FORCE(S), A VALUE OF A (TOTAL) TENSIONING FORCE APPLIED BY THE NEEDLE DRIVER

512 — DISPLAY, AT THE DISPLAY DEVICE OF THE TENSIONOMETER ASSEMBLY, THE VALUE OF THE TENSIONING FORCE

514 — COMPARE THE VALUE OF THE TENSIONING FORCE WITH ONE OR MORE THRESHOLD VALUES THAT DEFINE AN APPROPRIATE RANGE OF TENSIONING FORCE ASSOCIATED WITH A SUTURING TASK

516 — DISPLAY INFORMATION INDICATING THE COMPARISON OF THE VALUE OF THE TENSIONING FORCE WITH ONE OR MORE THRESHOLD VALUES

FIG. 8

SYSTEMS AND METHODS FOR A SUTURE TENSIONOMETER DEVICE

CROSS-REFERENCE TO RELATED APPLICATIONS

This is a U.S. Non-Provisional Patent Application that claims benefit to U.S. Provisional Patent Application Ser. No. 63/348,053 filed 2 Jun. 2022, which is herein incorporated by reference in its entirety.

FIELD

The present disclosure generally relates to surgical instruments, and in particular, to surgical instruments that aid in the closure of a wound by measuring the degree of tension applied to a suture during wound closure.

BACKGROUND

The closure of a surgical wound, such as after a laparotomy, can be particularly challenging. For example, pulling a stitch too tight when suturing the wound can cut off the blood supply around the wound and can cause necrosis. A loose stitch during wound closure, however, can prevent each side of the wound from properly connecting, thereby not facilitating complete healing of the wound. Current technologies allow a surgeon to test the tension created by a suture during wound closure after a stitch has already been sewn, but such technologies do not allow for real-time feedback while a stitch is being sewn. In addition, current technologies for testing the tension created by a suture during wound closure require the placement of implements through the loops defined by the suture, which may interfere with the healing process.

It is with these observations in mind, among others, that various aspects of the present disclosure were conceived and developed.

BRIEF DESCRIPTION OF THE DRAWINGS

FIG. 1A shows a side view of the device, FIG. 1B shows a cross-sectional view of a member of the needle driver with one embodiment of the tensionometer assembly, and FIG. 1C shows a top plan view of lateral forces being applied to the needle driver during a suturing task;

FIG. 3A shows a side view of the device, FIG. 3B shows a cross-sectional view of a member of the needle driver with one embodiment of the tensionometer assembly, and FIG. 3C shows a top plan view of lateral forces being applied to the needle driver during a suturing task;

FIG. 4A shows a side view of the device, FIG. 4B shows a first top plan view showing orientation of the tensionometer assembly when applying a tensioning force in a first lateral direction, and FIG. 4C shows a second top plan view showing orientation of the tensionometer assembly when applying a tensioning force in a second lateral direction;

FIGS. 5A-5G are a series of illustrations showing the tensionometer assembly of FIGS. 4A-4C without the needle driver, where FIG. 5A shows a first side view of the tensionometer assembly, FIG. 5B shows a second side view of the tensionometer assembly, FIG. 5C shows a top plan view of the tensionometer assembly, FIG. 5D shows a bottom plan view of the tensionometer assembly, and FIGS. 5E-5G respectively show cross-sectional side views of the tensionometer assembly taken along lines 5E-5E, 5F-5F, and 5G-5G of FIG. 5C;

FIG. 7A shows the display device being moveable along a member of the needle driver, FIG. 7B shows an enlarged view of the display device, and FIGS. 7C and 7D are sequential views showing removeable engagement of the display device with the member of the needle driver;

FIG. 8 is a process flow diagram showing a method for measuring tensioning force(s) by the devices of FIGS. 1A-7D.

Corresponding reference characters indicate corresponding elements among the view of the drawings. The headings used in the figures do not limit the scope of the claims.

DETAILED DESCRIPTION

Various embodiments of a suture tensionometer device for measuring the amount of tension applied to tensioning element such as a suturing needle or thread during closure of a surgical wound are disclosed herein. More specifically, a device as described herein may include a needle driver having a pair of jaws and a pair of handles operably connected by a pivotable joint, wherein the jaws are operable to swivel open and closed as the handles are concurrently opened and closed. The device can further include a tensionometer assembly that measures and displays values of tensioning force(s) applied by the needle driver. In one aspect, the suture tensionometer device is operable to measure a set of tensioning forces applied between one or more points along the device. During closure of a wound, the suture tensionometer device may be used to grasp a suture needle to push or pull the suture through the skin proximate to the wound while measuring and displaying a value of a tensioning force applied to the suture during wound closure.

Figure 1A:
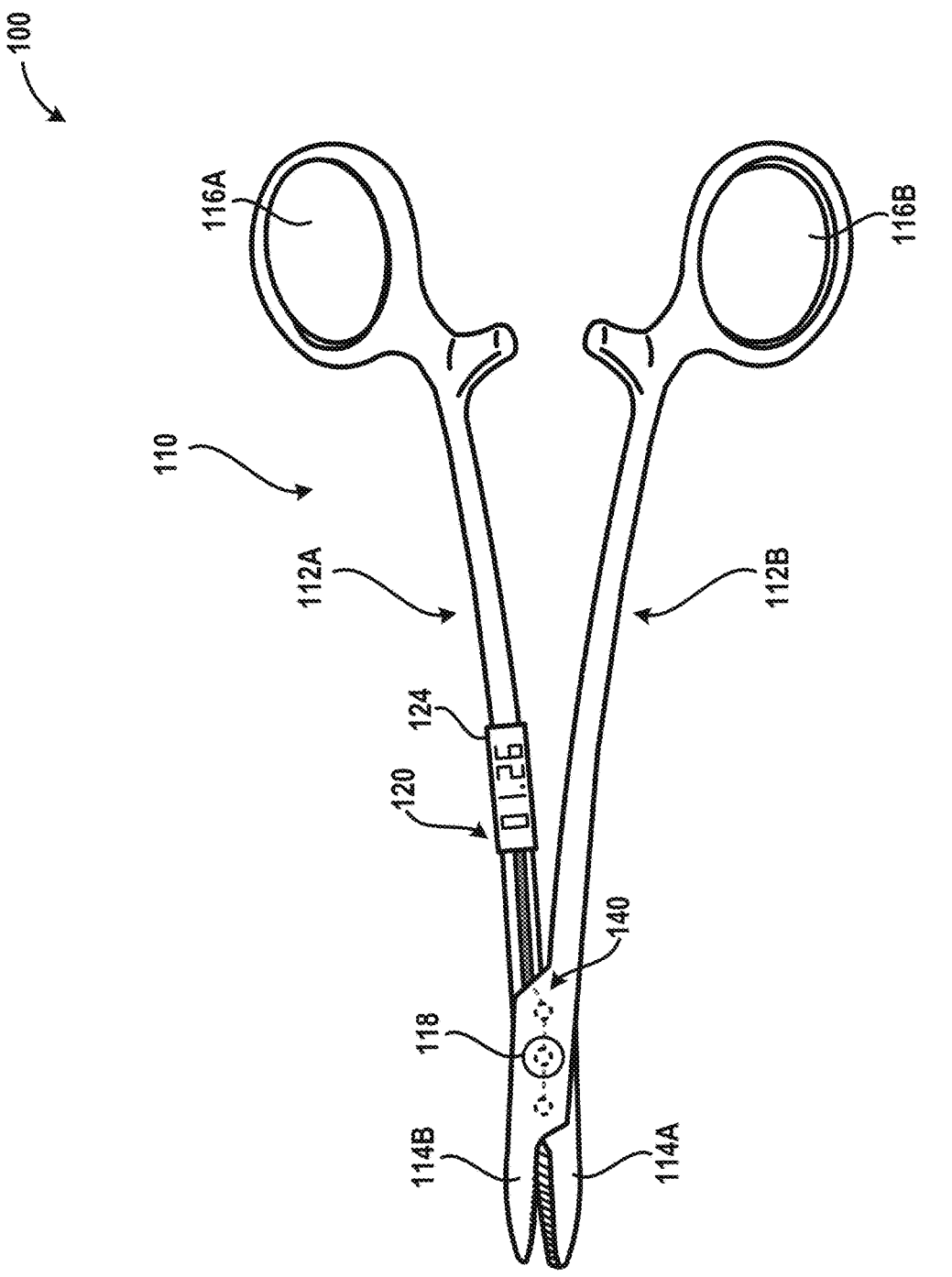
FIGS. 1A-1C are a series of illustrations showing a first embodiment of a device including a needle driver and a tensionometer assembly, where
Figures 1B, 1C:
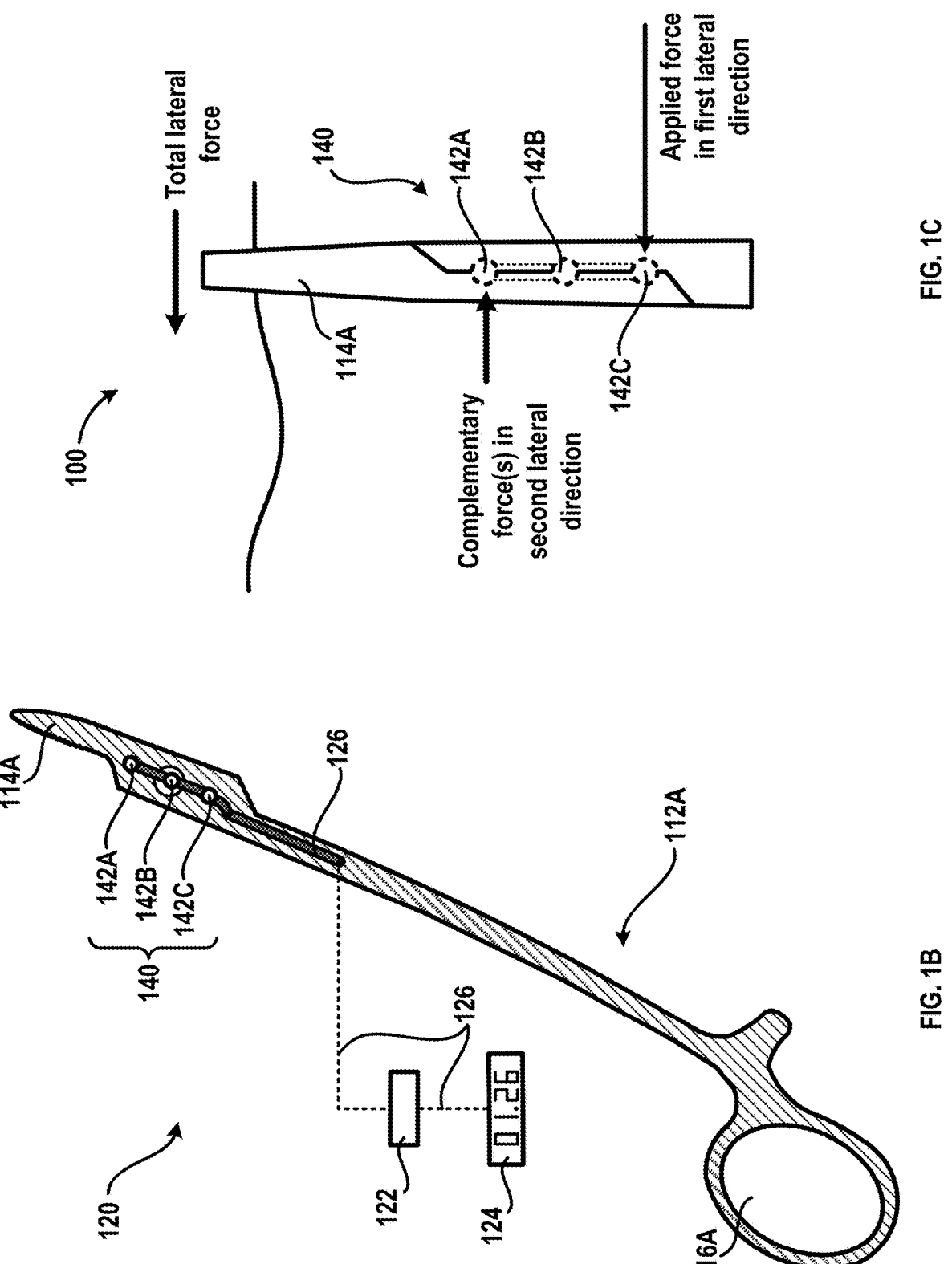

Referring to FIGS. 1A-1C, a suture tensionometer device (hereinafter, device 100) includes a needle driver 110 defining a first member 112A and a second member 112B as shown. The first member 112A and the second member 112B are crossed as shown in FIG. 1A and collectively define a pair of jaws (e.g., a first jaw member 114A and a second jaw member 114B) along a distal portion of needle driver 110. The first member 112A and the second member 112B can also collectively form a pair of handles (e.g., a first handle 116A and a second handle 116B) along a proximal portion of needle driver 110 as shown. In some embodiments, the first jaw member 114A and the first handle 116A both form portions of the first member 112A. Similarly, the second jaw member 114B and the second handle 116B both form portions of the second member 112B. As shown, the first member 112A and the second member 112B couple with one another in an overlapping or "crossed" arrangement at a pivotable joint 118.

Figure 6:
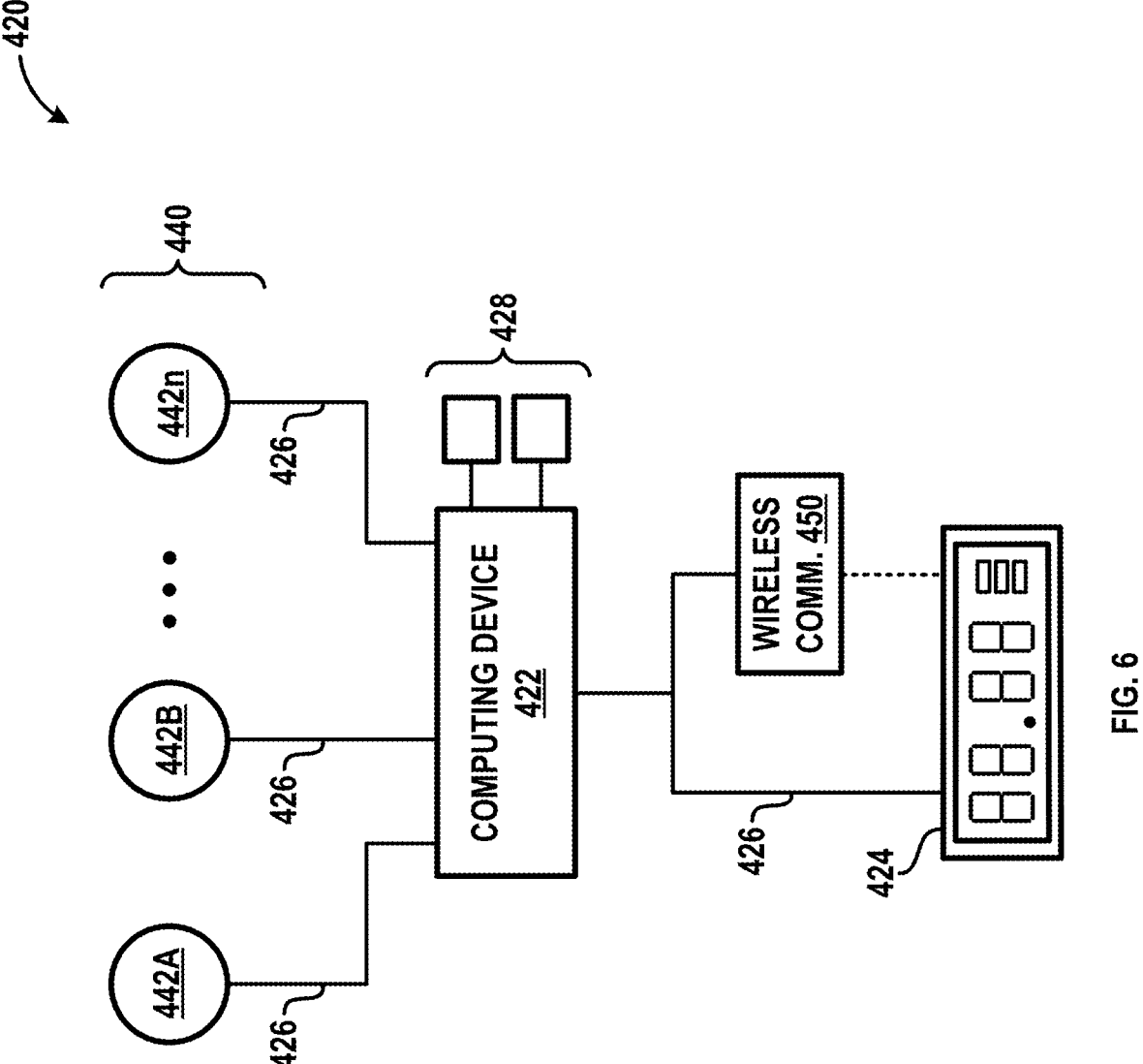
FIG. 6 is a simplified block diagram showing electronic components of a tensionometer assembly.
Figures 7A, 7B, 7C, 7D:
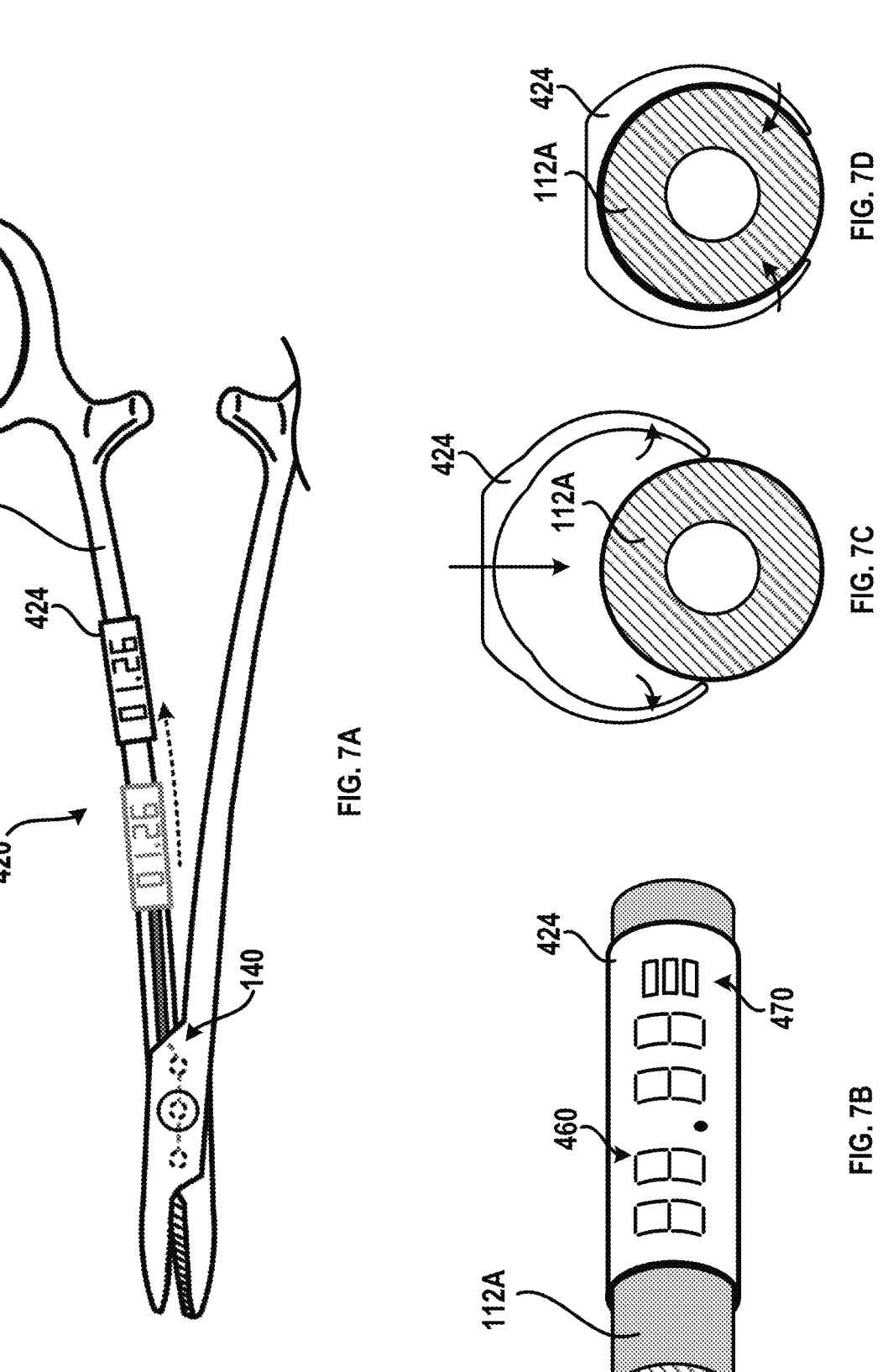
FIGS. 7A-7D are a series of illustrations showing a display device of the tensionometer assembly, where

In some embodiments, the needle driver 110 can include a tensionometer assembly 120 including a plurality of force-sensing elements in the form of a transducer array 140 for measuring a lateral tension force being applied by the needle driver 110 during a surgical task such as suturing. FIG. 1B shows an example arrangement of the tensionometer assembly 120 and transducer array 140 integrated within the first member 112A (or the second member 112B) of the needle driver 110. In this example, the tensionometer assembly 120 includes a computing device 122 in communication with a display device 124. The computing device 122 may be in a compact form with minimal hardware dedicated to the tasks involved with receiving and interpreting signals from the transducer array 140, calculating a force value based on the signals from the transducer array 140, and providing signals to the display device 124 for displaying the force value to a practitioner. The transducer array 140, computing device 122, and display device 124 can communicate with one another through wired or wireless connections, e.g., through connection elements 126. FIGS. 6-7C discussed herein provide additional information about various hardware components of the tensionometer assembly 120. In other examples, the transducer array 140 and/or display device 124 can be purely mechanical in nature, or can include a combination of electromechanical elements for measuring and displaying force values.

With continued reference to FIGS. 1B and 1C, the transducer array 140 can include a plurality of transducers for measuring force values at different positions along the needle driver 110, including a first transducer 142A, a second transducer 142B, and a third transducer 142C. In this embodiment, the first transducer 142A, second transducer 142B, and third transducer 142C can be arranged equidistant along a common plane (e.g., along a direction of elongation of the needle driver 110) near the pivotable joint 118 of the needle driver 110 as shown, with the second transducer 142B being in alignment with the pivotable joint 118. The first transducer 142A can be distal to the pivotable joint 118 and the third transducer 142C can be proximal to the pivotable joint 118. The transducer array 140 can be encapsulated between the first member 112A and the second member 112B.

FIG. 1C is an enlarged view showing arrangement of the transducer array 140 with respect to various forces including an applied force along a first lateral direction (e.g., as applied by a practitioner). In this example, the third transducer 142C measures the applied force along the first lateral direction, the first transducer 142A measures complementary force(s) in a second lateral direction, and the second transducer 142B measures an intermediate force to serve as a "reference point" between the first transducer 142A and the third transducer 142C. Based on the value(s) of tensioning force measured by the first transducer 142A, the second transducer 142B, and the third transducer 142C, the computing device 122 determines a total amount of tensioning force (e.g., lateral tension) that is being applied to a suture when the needle driver 110 is pulled in a generally lateral direction during a suturing task. The amount of tensioning force can be displayed to a practitioner within the surgical environment and/or can be collected and stored for analysis.

FIGS. 2A-2D show use cases for one embodiment of the device 100 for measuring an amount of tensioning force being applied during a suturing task. The jaws of the needle driver 110 (e.g., first jaw member 114A and second jaw member 114B shown in FIG. 1A) can collectively receive and transfer a tensioning force to a tensioning element such as a suturing needle 10 (FIG. 1C) and/or suturing thread 12 therebetween. The suturing needle 10 can be coupled to the suturing thread 12 for suturing two sides (e.g., a first side 2A and a second side 2B) of a surgical wound 2 together.

Figure 2B:
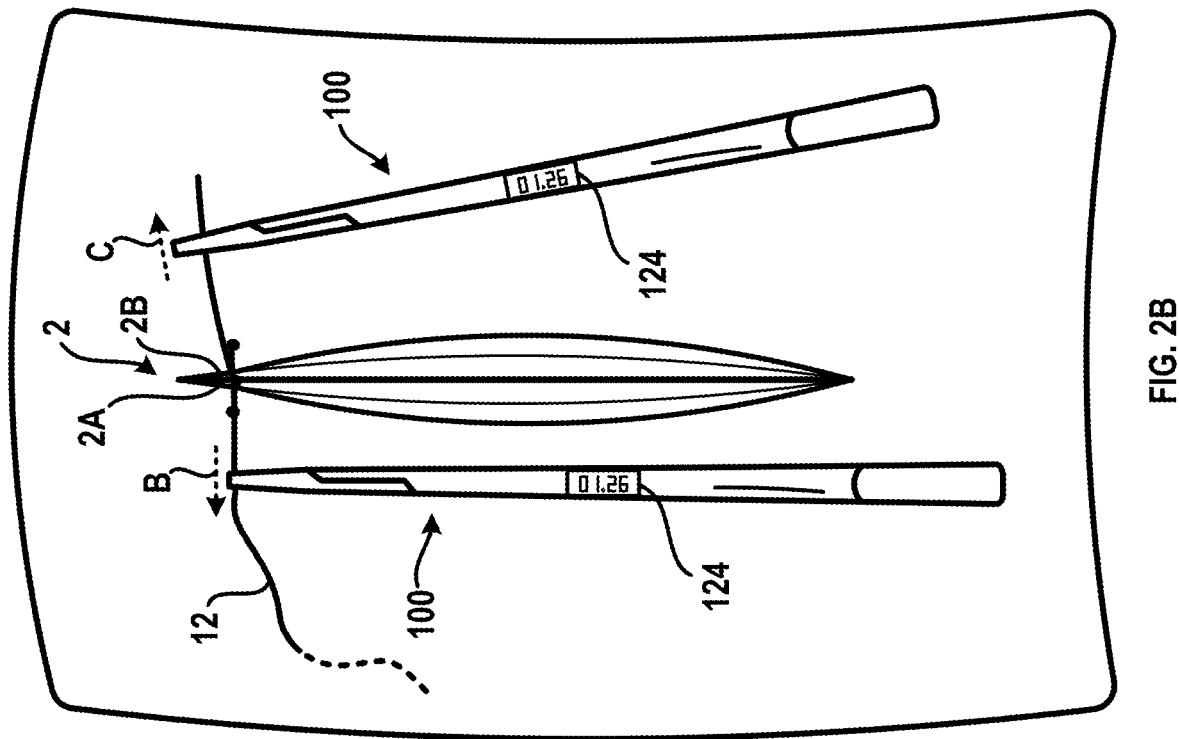
FIGS. 2A-2D are a series of sequential illustrations showing execution of various suturing tasks using the device of FIGS. 1A-1C.
Figure 2A:
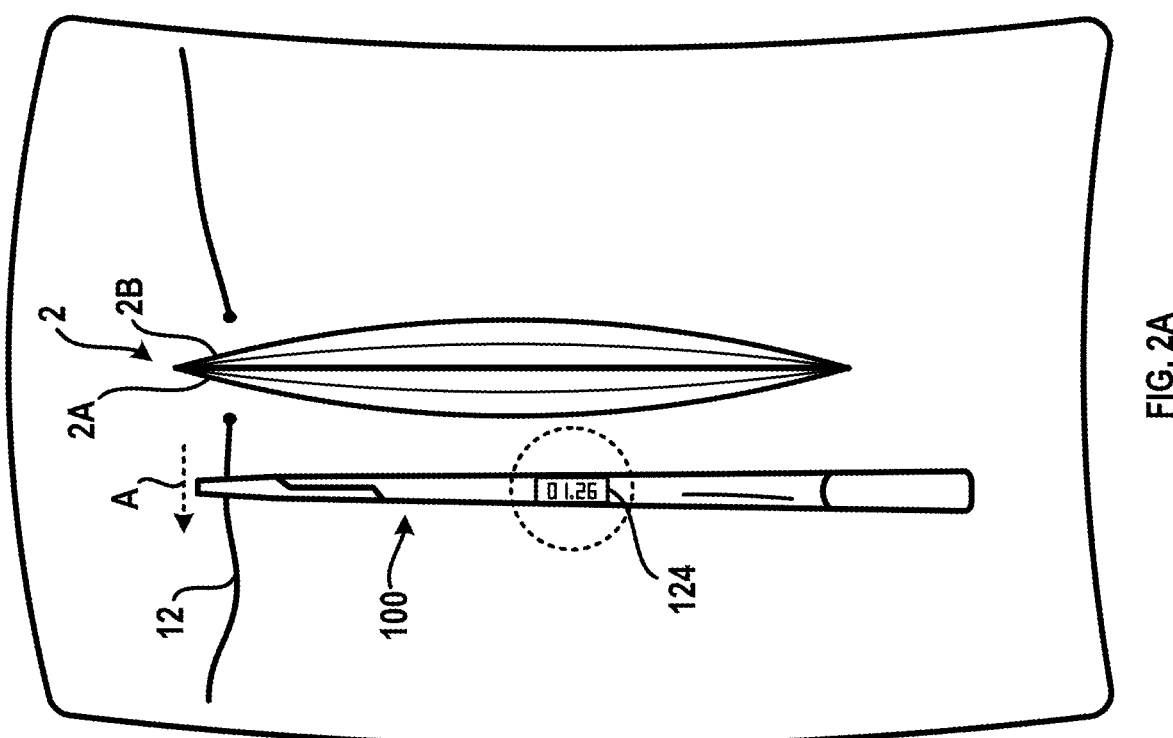

FIG. 2A shows one example where the suturing thread 12 has been passed between the first side 2A and the second side 2B of the surgical wound 2 for a first suture. At this step, the device 100 can be used to pull the suturing thread 12 "taut" to draw the first side 2A and the second side 2B of the surgical wound 2 together—it is imperative that sufficient tension is applied in order to effectively draw the first side 2A and the second side 2B together without over-tensioning. As such, the device 100 is shown applying a first total tensioning force A in a first lateral direction to the suturing thread 12. The tensionometer assembly 120 determines the value of the first total tensioning force A and displays the value at the display device 124 as shown.

FIG. 2B shows the suturing thread 12 being tied between the first side 2A and the second side 2B of the surgical wound 2 to complete a first suture. At this step, one or more device(s) 100 can be used to pull the suturing thread 12 "taut" to draw the first side 2A and the second side 2B of the surgical wound 2 together and complete the knot. As such, one device 100 is shown applying a second total tensioning force B to the suturing thread 12 in the first lateral direction at the first side 2A, and the tensionometer assembly 120 determines the value of the second total tensioning force B and displays the value at the display device 124 as shown. Likewise, another device 100 is shown applying a third total tensioning force C to the suturing thread 12 in a second lateral direction at the second side 2B, and the tensionometer assembly 120 determines the value of the third total tensioning force C and displays the value at the display device 124 as shown.

Figure 2D:
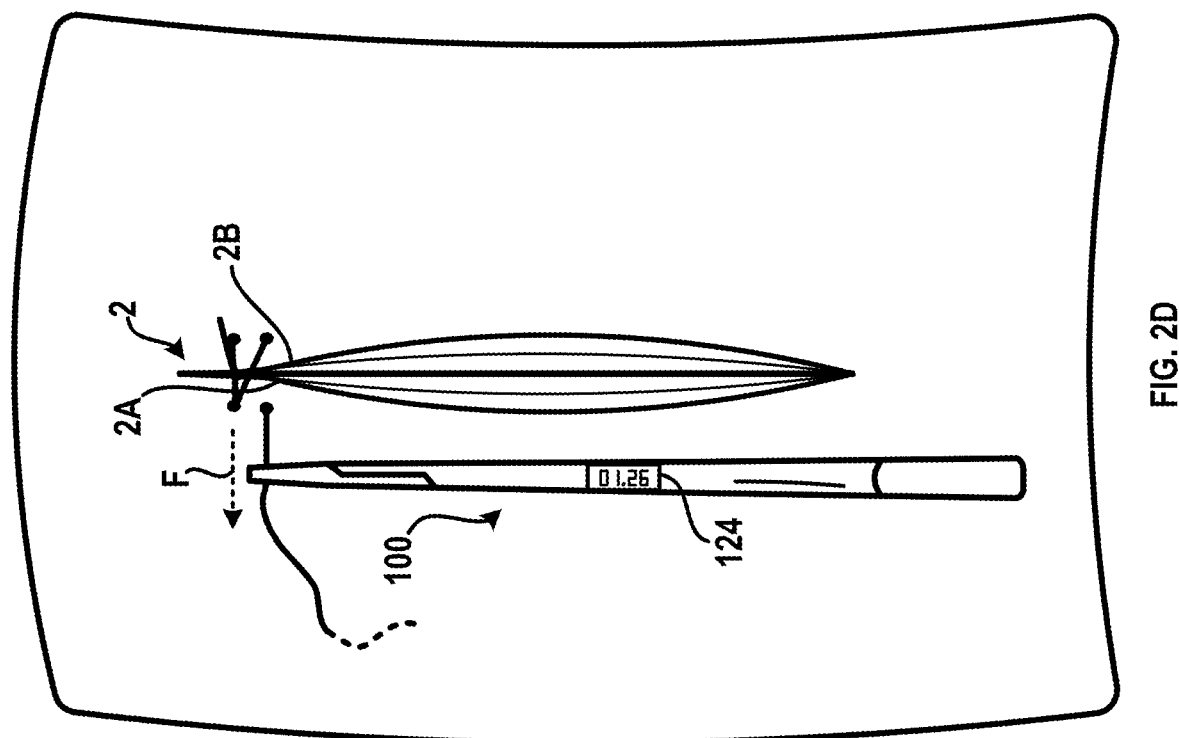
Figure 2C:
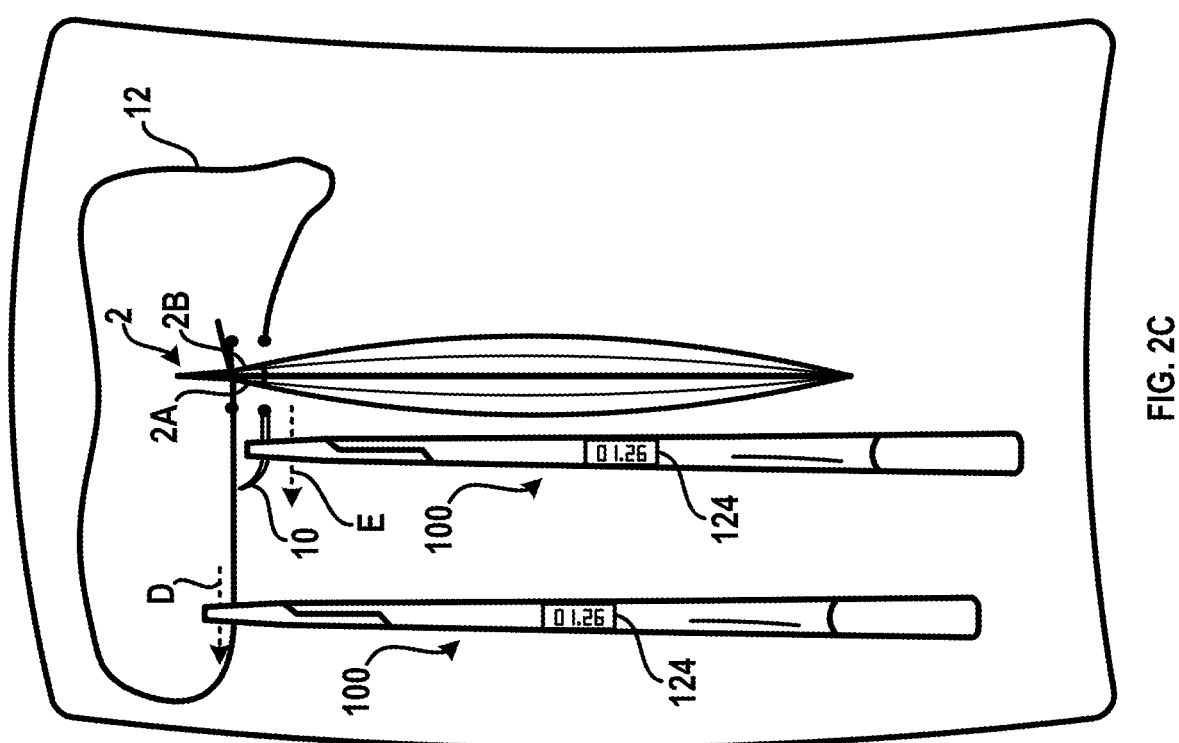

FIG. 2C shows formation of a second suture along the surgical wound 2. In this example, one device 100 is used to capture and pull the suturing thread 12 taut along the first lateral direction and applies a fourth total tensioning force D to the suturing thread 12 in the first lateral direction at the first side 2A to maintain appropriate tension on the first suture. The tensionometer assembly 120 determines the value of the fourth total tensioning force D and displays the value at the display device 124 as shown. Simultaneously, another device 100 is shown gripping the suturing needle 10 to form the second suture. The device 100 applies a fifth total tensioning force E to pull the suturing needle 10 in the first lateral direction at the first side 2A to pull the suturing thread between the second side 2B and the first side 2A. Likewise, the tensionometer assembly 120 determines the value of the fifth total tensioning force E and displays the value at the display device 124 as shown.

FIG. 2D shows a further step following the step of FIG. 2C where the suturing thread 12 has been passed between the first side 2A and the second side 2B of the surgical wound 2 for the second suture. At this step, the device 100 can be used to pull the suturing thread 12 "taut" to further draw the first side 2A and the second side 2B of the surgical wound 2 together—it is imperative that sufficient tension is applied in order to effectively draw the first side 2A and the second side 2B together without over-tensioning. As such, the device 100 is shown applying a sixth total tensioning force F in the first lateral direction to the suturing thread 12. The tensionometer assembly 120 determines the value of the sixth total tensioning force F and displays the value at the display device 124 as shown.

Figure 3A:
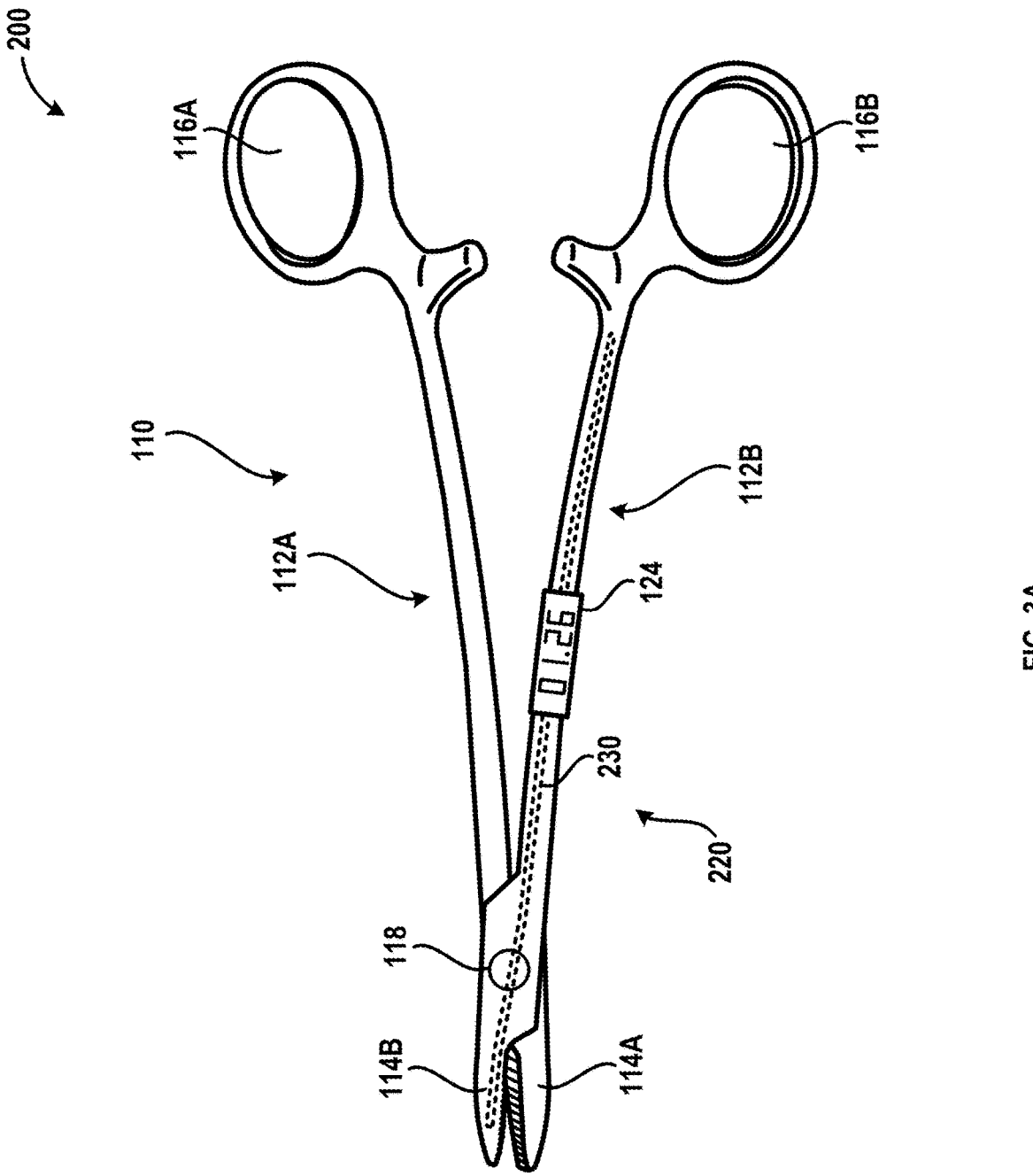
FIGS. 3A-3C are a series of illustrations showing a second embodiment of a device including a needle driver and a tensionometer assembly, where
Figure 3C:
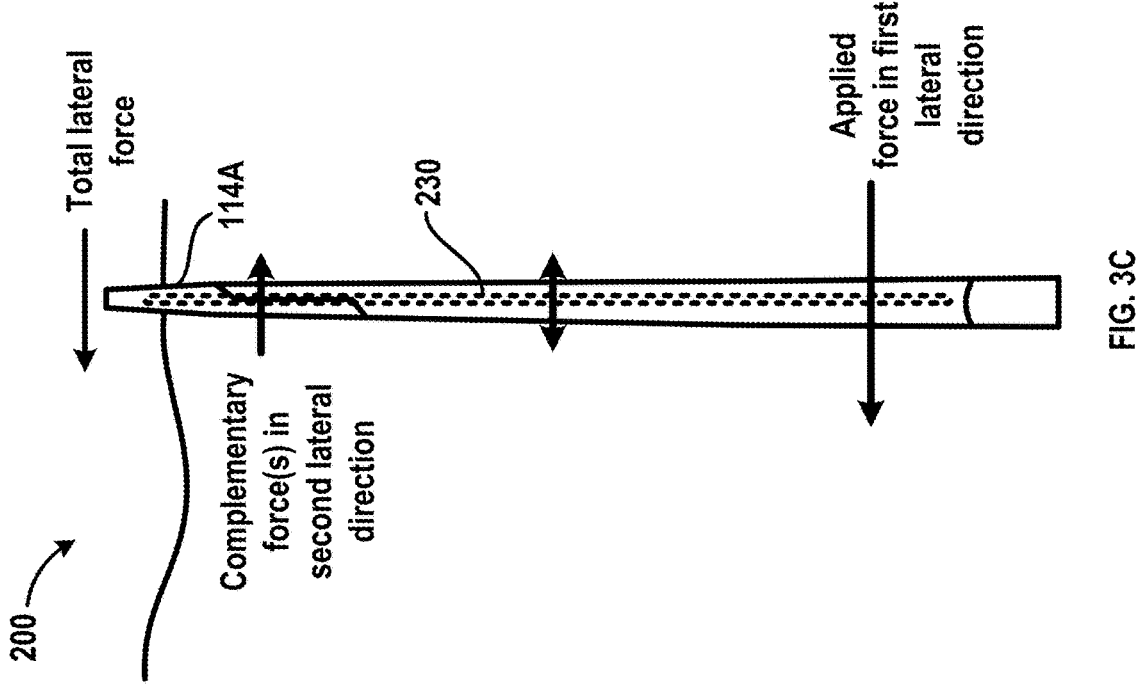
Figure 3B:
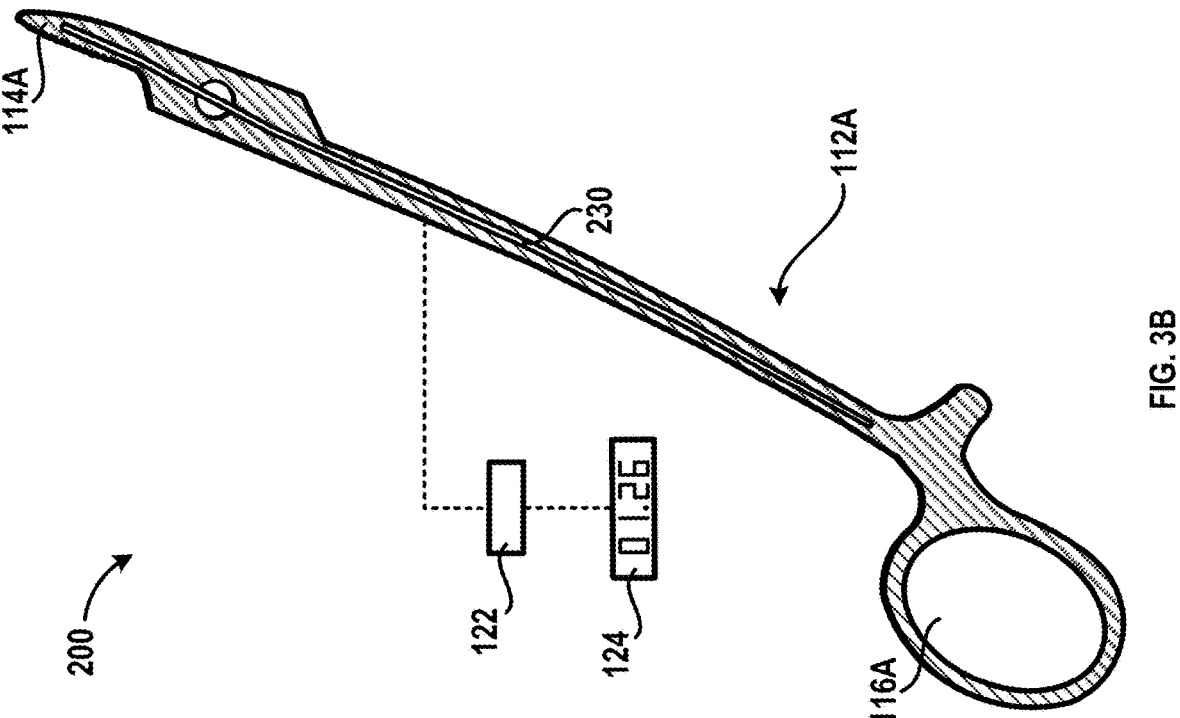

While the examples of FIGS. 2A-2D are shown and discussed in terms of the device 100 shown in FIGS. 1A-1C, these examples can be similarly applied to alternate embodiments of device 100 discussed herein with reference to a device 200 shown in FIGS. 3A-3C, and a device 300 shown in FIGS. 4A-5G.

FIGS. 3A-3C show the device 200 including the needle driver 110 having a tensionometer assembly 220. Similar to that of the device 100 shown in FIGS. 1A-2D, the needle driver 110 of device 200 can be similar to a conventional needle driver 110 including the first member 112A having the first jaw member 114A and the first handle 116A, and the second member 112B having the second jaw member 114B and the second handle 116B. The first member 112A and the second member 112B are crossed at pivotable joint 118.

The tensionometer assembly 220 can include a force-sensing element in the form of sensing rod 230 that is operable for measuring an amount of laterally applied force applied from one location on the sensing rod 230 to a separate location on the sensing rod 230 and positioned within or along the first member 112A (and/or the second member 112B) for measuring a total tensioning force applied by the device 200. The sensing rod 230 can align with a direction of elongation of the first member 112A or the second member 112B, and can extend substantially along the length of the first member 112A (and/or the second member 112B) as shown in the cutaway view of FIG. 3B. Similarly, the sensing rod 230 can be in operative communication with the computing device 122 and display device 124 for measuring and displaying a value of the total tensioning force.

FIG. 3C is an enlarged view showing arrangement of the sensing rod 230 with respect to various forces including an applied force along the first lateral direction (e.g., as applied by a practitioner). In this example, the sensing rod 230 measures the applied force along the first lateral direction, and can also measure complementary force(s) along the second lateral direction and an intermediate force to serve as a "reference point". Based on the tensioning force values measured by the sensing rod 230, the computing device 122 determines a total amount of tensioning force (e.g., lateral tension) that is being applied to a suture when the needle driver 110 is pulled in a generally lateral direction during a suturing task. The amount of tensioning force can be displayed to a practitioner within the surgical environment and/or can be collected and stored for analysis.

Figure 4A:
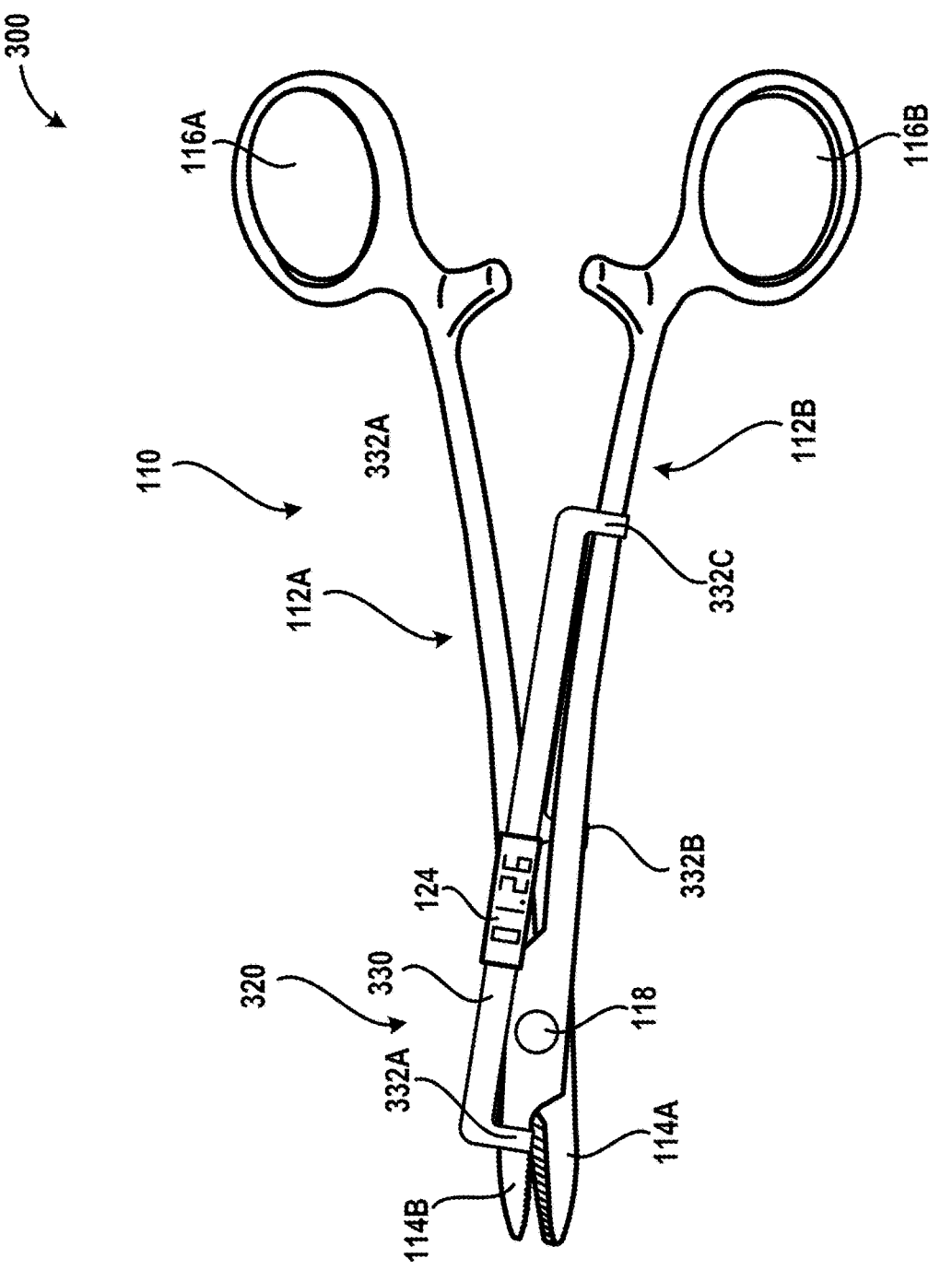
FIGS. 4A-4C are a series of illustrations showing a third embodiment of a device including a needle driver and a tensionometer assembly, where
Figure 4C:
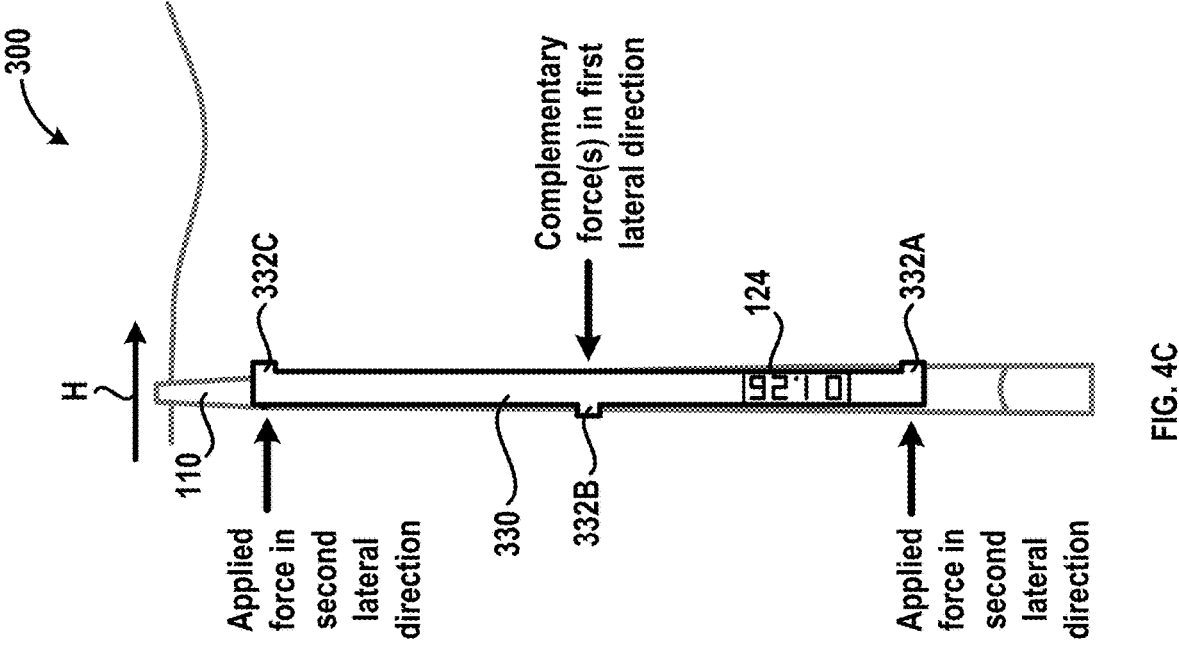
Figure 4B:
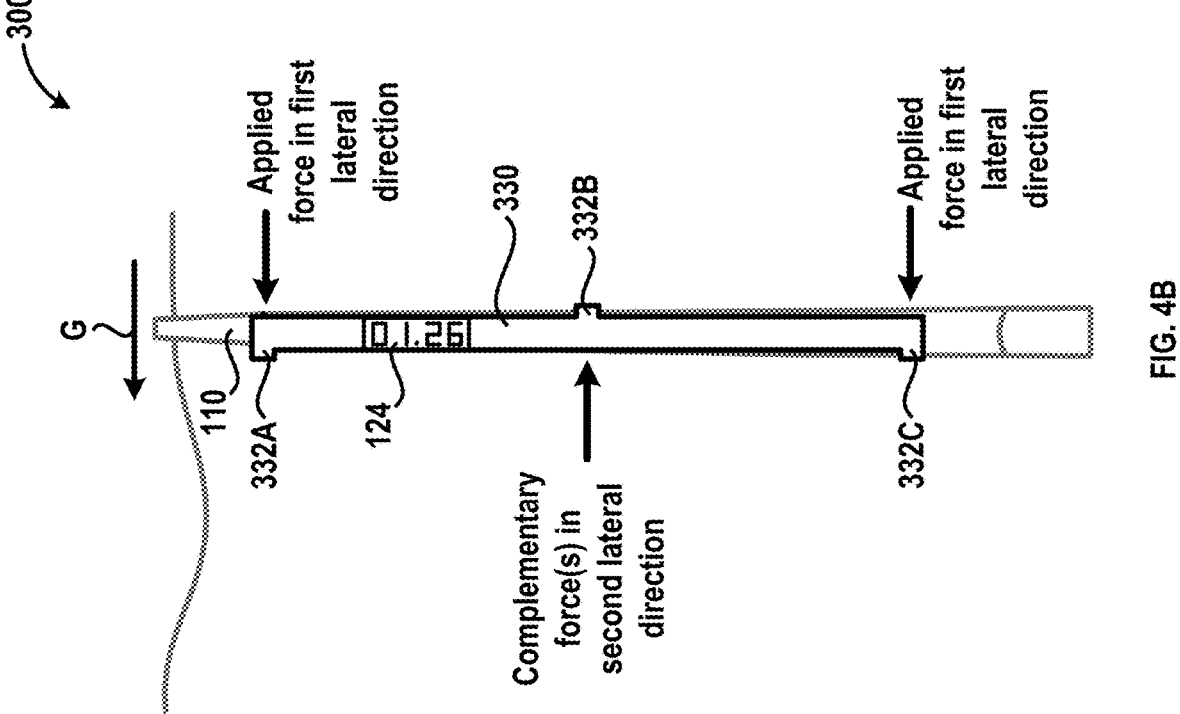

FIGS. 4A-4C show the device 300 including the needle driver 110 having a tensionometer assembly 320. Similar to that of the device 100 shown in FIGS. 1A-2D and the device 200 shown in FIGS. 3A-3C, the needle driver 110 of device 300 can be similar to a conventional needle driver 110 including the first member 112A having the first jaw member 114A and the first handle 116A, and the second member 112B having the second jaw member 114B and the second handle 116B. The first member 112A and the second member 112B are crossed at pivotable joint 118.

The tensionometer assembly 320 can include a clamp device 330 including a first prong 332A, a second prong 332B, and a third prong 332C configured for engagement with the first member 112A or the second member 112B of the needle driver 110 as shown. FIGS. 5A-5G show various views of the clamp device 330. The clamp device 330 contacts the first member 112A or second member 112B at a first prong 332A, a second prong 332B, and a third prong 332C, which can be spaced equidistant from one another. The clamp device 330 can be removably coupled to the needle driver 110.

Importantly, first prong 332A and third prong 332C contact a first side of the first member 112A or second member 112B that follows a direction of lateral movement of the needle driver, and second prong 332B contacts a second side of the first member 112A or second member 112B that opposes the direction of lateral movement of the needle driver. As the needle driver 110 is pulled from the handle(s) 116A and 116B in a lateral direction, the needle driver 110 will naturally remain rigid, and the force applied at the handle(s) 116A and 116B will translate to a tensioning force applied at the jaw members 114A and 114B. The clamp device 330 is operable to detect forces acting on different points of the needle driver 110 between the first prong 332A, a second prong 332B, and a third prong 332C and calculate the total tensioning force being applied on a suture at the jaw members 114A and 114B of the needle driver 110. The clamp device 330 may be retrofitted onto an existing needle driver or may be manufactured as an integral part of the needle driver 110.

For example, FIG. 4B shows one configuration where the path of lateral movement follows a first lateral direction (e.g., to the "left") with a total applied tensioning force G being applied from the "right" side of the needle driver 110. The clamp device 330 is positioned such that the first prong 332A and third prong 332C are along the side of the needle driver 110 that corresponds with the path of lateral movement (e.g., the "left" side), which is opposite from the side that the applied force originates from (e.g., the "right" side). The second prong 332B is along the opposite side from the first prong 332A and third prong 332C, also interpreted as along the side that the applied force originates from (e.g., the "right" side). The first prong 332A and third prong 332C can include transducers or other elements that enable collective measurement of tensioning forces that are applied along the first lateral direction. Likewise, the second prong 332B can be include transducers or other elements that enable measurement of complementary force(s) along the second lateral direction.

Conversely, FIG. 4C shows another configuration where the path of lateral movement follows a second lateral direction (e.g., to the "right") with a total applied tensioning force H being applied from the "left" side of the needle driver 110. The clamp device 330 is positioned such that the first prong 332A and third prong 332C are along the side of the needle driver 110 that corresponds with the path of lateral movement (e.g., the "right" side), which is opposite from the side that the applied force originates from (e.g., the "left" side). The second prong 332B is along the opposite side from the first prong 332A and the third prong 332C, also interpreted as along the side that the applied force originates from (e.g., the "left" side). The first prong 332A and third prong 332C can include transducers or other elements that enable collective measurement of tensioning forces that are applied along the second lateral direction. Likewise, the second prong 332B can be include transducers or other elements that enable measurement of complementary force(s) along the third lateral direction. In the example shown, and relative to the preceding example of FIG. 4B, the first prong 332A and the third prong 332C are "flipped" as the same clamp device 330 could be used for either direction. Importantly, the clamp device 330 includes one or more force-sensing elements that can be in the form of a first transducer 342A, a second transducer 342B, and a third transducer 342C that collectively measure the total tensioning force being applied.

FIGS. 5A-5G show the clamp device 330 decoupled from the needle driver 110 of FIGS. 4A-4C. FIG. 5A shows a first side view of the clamp device 330 with the first prong 332A and third prong 332C being "closer" to the viewer than the second prong 332B. FIG. 5B shows a second side view of the clamp device 330 with the second prong 332B being "closer" to the viewer than the first prong 332A and third prong 332C. In these examples, the first prong 332A includes the first transducer 342A, the second prong 332B includes the second transducer 342B, and the third prong 332C includes the third transducer 342C that collectively measure values of one or more components of the total tensioning force being applied by the needle driver 110. Further, the clamp device 330 can include a computing device (e.g., computing device 422 shown in FIG. 6) for receiving measurements from the one or more force-sensing elements, determining the value of the total tensioning force and for applying control signals to the display device 124 for displaying the value of the total tensioning force.

FIGS. 5C and 5D respectively show top plan and bottom plan views of the clamp device 330. The clamp device 330 can form an elongated body having a spine 336 with the first prong 332A and third prong 332C extending from a first lateral side of the spine 336 at respective first and second free ends of the spine 336, and the second prong 332B extending from a second lateral side of the spine 336 along a midsection of the spine 336 as shown. The clamp device 330 can include the display device 124 along the spine 336 and facing the practitioner when in use. FIGS. 5E, 5F, and 5G respectively show cross-sectional views of the clamp device 330 taken along lines 5E-5E, 5F-5F, and 5G-5G that correspond with the first prong 332A, second prong 332B, and third prong 332C. In the views of FIGS. 5E, 5F, and 5G, the first transducer 342A, the second transducer 342B, and the third transducer 342C are shown connecting to one another and the computing device (see FIG. 6) through traces or connection elements that can be encapsulated or otherwise housed within the spine 336. In other examples, the first transducer 342A, the second transducer 342B, the third transducer 342C and/or display device 124 can be purely mechanical in nature, or can include a combination of electromechanical elements for measuring and displaying force values.

FIG. 6 shows various electronic components of a tensionometer assembly 420 (e.g., which can be any one of tensionometer assemblies 120, 220, and/or 320) according to the embodiments outlined herein. The tensionometer assembly 420 includes a computing device 422 that receives signals for measuring forces from a transducer array 440, which can include transducers 442A-442n as shown. Transducers 442A-442n can be arranged as shown with respect to transducers 142A-142C of FIGS. 1A-1C and/or transducers 342A-342C of FIGS. 5A-5G. With respect to the sensing rod 230 of FIGS. 3A-3C, the sensing rod 230 can similarly include one or more transducers for measuring and interpreting forces applied at the needle driver 110 (FIGS. 1A-4C). The transducer array 440 can connect with the computing device 422 by one or more wires 426 or by another connection method. In some examples, computing device 422 can also receive input through input element(s) 428, which can enable a practitioner to perform various actions such as "zeroing" when the device 100 is to prevent inaccuracies due to sensor drift.

The computing device 422 can be operable to receive signals or other information indicative of force measurement(s) from the transducer array 440 and calculate a value of a total tensioning force (tensile force) being exerted by the device (e.g., device 100, 200 and/or 300) on a suture. In some examples, the computing device 422 can apply control signal(s) to a display device 424 (which can be display device 124 discussed herein with reference to FIGS. 1A-1C, 3A-3C and 4A-5C) for displaying the value of the total tensioning force. The display device 424 can receive control signal(s) from the computing device 422 by wired or wireless connection. For wireless connection, the tensionometer assembly 420 can include a wireless communications component 450 for communicating control signal(s) between the computing device 422 and the display device 424. In some examples, the transducer array 440 can also communicate with the computing device 422 by wireless connection through the wireless communications component 450.

In the example of FIG. 6, and as can be applied to other embodiments herein, the computing device 422 can compare the value of the total tensioning force with one or more thresholds to determine if the detected force is appropriate. For example, if the detected force is too "low" or below a "minimum" threshold, the computing device 422 may apply control signal(s) to the display device 424 to indicate to the practitioner that the applied tensioning force is too low and that the practitioner may need to apply more force to ensure that the tension held by the suture is appropriate. If the detected force is appropriate and above the "minimum" threshold but below a "maximum" threshold, the computing device 422 may apply control signal(s) to the display device 424 to indicate to the practitioner that the applied force is appropriate. The computing device 422 and display device 424 may provide further refinement by indicating how close the practitioner is to a maximum or minimum threshold force value (e.g., to avoid sutures that may be somewhat loose or somewhat tight). If the detected force is too "high" or above a "maximum" threshold, the computing device 422 may apply control signal(s) to the display device 424 to indicate to the practitioner that the applied force is too high and that the practitioner may need to reduce the amount of applied force to ensure that the tension held by the suture is appropriate.

In addition, the computing device 422 may also include a processing element (see FIG. 9) for various functionalities including data collection, and force calculation, and generating/applying control signals to the display device 424. In other embodiments, the computing device 422 may be housed outside the needle driver 110 and can be placed on a nearby table or any location the user finds convenient. In other embodiments, the computing device 422 and/or display device 424 may be worn around a wrist of the practitioner or incorporated into a smart watch application.

The computing device 422 can use known formulae and other methods for determining the amount of applied tensioning force on a suture based on the force measurements taken by the transducer array 440 at different points along the device 100, 200 and/or 300. In some examples, the computing device 422 can display and/or toggle a unit of measurement (e.g., newtons, Pascal, pounds, (kilo) grams, etc.).

FIGS. 7A-7D show example embodiments of the display device 424 that communicates with the computing device 422 for displaying a total tensioning force being exerted by the device 100, 200 or 300. FIG. 7A shows the display device 424 of the tensionometer assembly 420 being moveable along the first member 112A of the needle driver 110 of FIGS. 1A-1C. This arrangement can be enabled by the wireless arrangement discussed herein with reference to FIG. 6. FIG. 7B shows one embodiment of the display device 424 being positionable along the first member 112A. The display device 424 can be of a compact form so as not to interfere with surgical tasks. In this example, the display device 424 is curved around the first member 112A, although other embodiments of the display device 424 can be of a different shape. In some examples, the display device 424 may be embedded within the first member 112A (or the second member 112B). Further, FIG. 7B shows a digital display element 460, which can be a seven-segment display or by another modality, and can in some examples include backlighting to improve visibility. In a further embodiment, the backlighting may vary in color and/or may be selectable, depending on factors such as: practitioner preference, the value of tensioning force, or a range that the value falls within (e.g., the backlighting may be green if the measured force is appropriate, blue if too low, red if too high, etc.). In other examples, backlighting may be limited or restricted to avoid certain colors that may interfere with surgical functionalities and devices such as those relying on certain wavelengths of light. The display device 424 can also include additional display element(s) 470 to indicate, for example, units of measurement being shown or to indicate a range that the value of tensioning force falls within. FIGS. 7C and 7D show the display device 424 being removably coupled to the first member 112A in a snap-fit engagement.

Methods

FIG. 8 shows a method 500 for measuring a total force exerted by the device(s) 100, 200, and 300 during a surgical task. The method 500 shows steps that correlate with the concepts outlined herein with respect to FIGS. 1A-7D. The functions performed in the processes and methods may be implemented in differing order. Furthermore, the outlined steps and operations are provided as examples, and some of the steps and operations may be optional, combined into fewer steps and operations, or expanded into additional steps and operations without detracting from the essence of the disclosed embodiments.

Step 502 of method 500 includes coupling a tensionometer assembly with a needle driver, the tensionometer assembly including: one or more force-sensing elements operable for measuring a value of the tensioning force being applied by the needle driver; and a display device in communication with the force-sensing elements and being operable to display the value of the tensioning force. In examples where the tensionometer assembly includes a clamp device such as clamp device 330 shown in FIGS. 4A-5G, this step can include positioning the clamp device along the first member or the second member of the needle driver such that: (1) the first prong and the second prong of the clamp device contact a first side of the first member or the second member that follows a direction of lateral movement of the needle driver; and (2) the second prong of the clamp device contacts a second side of the first member or the second member that opposes a direction of lateral movement of the needle driver.

Step 504 of method 500 includes applying, by the needle driver, a tensioning force to a tensioning element (e.g., suturing thread or a suturing needle). Step 506 of method 500 includes measuring, by the force-sensing elements of the tensionometer assembly, the value of the tensioning force. In some examples, the measurements captured by the force-sensing elements include one or more values of one or more forces that can be used to determine the value of the (total) tensioning force, Step 508 of method 500 includes accessing, at a processor of the tensionometer assembly in communication with a memory, the value(s) of the tensioning force(s) as measured at the force-sensing elements positioned along the needle driver, the force-sensing elements being in communication with the processor. Step 510 of method 500 includes determining, based on the value(s) of the tensioning force(s) as measured at the force-sensing elements, a value of a (total) tensioning force applied by the needle driver. Step 512 of method 500 includes displaying, at the display device of the tensionometer assembly in communication with the processor, the value of the (total) tensioning force.

In some examples, step 514 of method 500 includes comparing the value of the total tensioning force with one or more threshold values that define an appropriate range of tensioning force associated with a suturing task. Step 516 of method 500 can include displaying information reflecting the comparison of the value of the (total) tensioning force with one or more threshold values.

Computing Device

Figure 9:
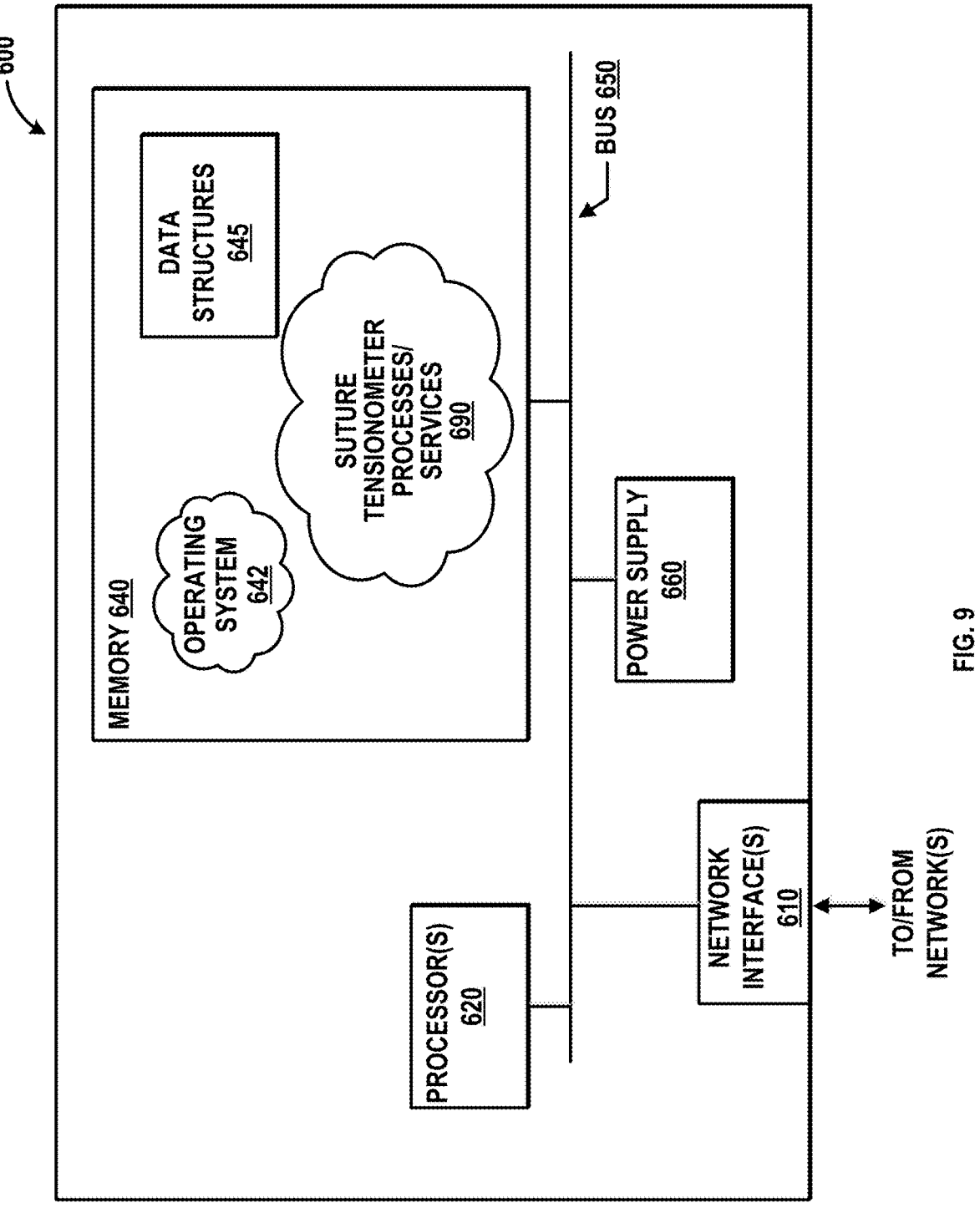
FIG. 9 is a simplified diagram showing an exemplary computing system for implementation of the devices and method of FIGS. 1A-8.

FIG. 9 is a schematic block diagram of a computing device 600 that may be used with one or more embodiments described herein, e.g., as computing device 122 shown in FIGS. 1B and 3B and/or as computing device 422 shown in FIG. 6.

Computing device 600 comprises one or more network interfaces 610 (e.g., wired, wireless, PLC, etc.), at least one processor 620, and a memory 640 interconnected by a system bus 650, as well as a power supply 660 (e.g., battery, plug-in, etc.).

Network interface(s) 610 include the mechanical, electrical, and signaling circuitry for communicating data over the communication links coupled to a communication network. Network interfaces 610 are configured to transmit and/or receive data using a variety of different communication protocols. As illustrated, the box representing network interfaces 610 is shown for simplicity, and it is appreciated that such interfaces may represent different types of network connections such as wireless and wired (physical) connections. Network interfaces 610 are shown separately from power supply 660, however it is appreciated that the interfaces that support PLC protocols may communicate through power supply 660 and/or may be an integral component coupled to power supply 660.

Memory 640 includes a plurality of storage locations that are addressable by processor 620 and network interfaces 610 for storing software programs and data structures associated with the embodiments described herein. In some embodiments, computing device 600 may have limited memory or no memory (e.g., no memory for storage other than for programs/processes operating on the device and associated caches). Memory 640 can include instructions executable by the processor 620 that, when executed by the processor 620, cause the processor 620 to implement aspects of the device(s) 100, 200 and 300 and the method 500 outlined herein.

Processor 620 comprises hardware elements or logic adapted to execute the software programs (e.g., instructions) and manipulate data structures 645. An operating system 642, portions of which are typically resident in memory 640 and executed by the processor, functionally organizes computing device 600 by, inter alia, invoking operations in support of software processes and/or services executing on the device. These software processes and/or services may include suture tensionometer processes/services 690, which can include aspects of method 500 and/or implementations of various modules described herein. Note that while suture tensionometer processes/services 690 is illustrated in centralized memory 640, alternative embodiments provide for the process to be operated within the network interfaces 610, such as a component of a MAC layer, and/or as part of a distributed computing network environment.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules or engines configured to operate in accordance with the techniques herein (e.g., according to the functionality of a similar process). In this context, the term module and engine may be interchangeable. In general, the term module or engine refers to model or an organization of interrelated software components/functions. Further, while the suture tensionometer processes/services 690 is shown as a standalone process, those skilled in the art will appreciate that this process may be executed as a routine or module within other processes.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, solid state memory devices, flash memory, USB devices provided with non-volatile memory, networked storage devices, and so on.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A device, comprising:
a needle driver including a first member and a second member joined at a connection, the needle driver being operable to capture a tensioning element; and
a tensionometer assembly in operative association with the needle driver, the tensionometer assembly including:
a plurality of force-sensing elements, each positioned along the first member and including:
a first force-sensing element positioned at a first longitudinal location along the first member distal of the connection;
a second force-sensing element positioned at a second longitudinal location along the first member coincident with the connection; and
a third force-sensing element positioned at a third longitudinal location along the first member proximal of the connection;
the plurality of force-sensing elements collectively measuring a lateral force component acting on the first member perpendicular to a longitudinal axis collectively defined by the first member and the second member, wherein the second force-sensing element serves as a reference between the first force-sensing element and the third force-sensing element.

2. The device of claim 1, the plurality of force-sensing elements including a plurality of transducers positioned along the first member or the second member of the needle driver.

3. The device of claim 1, the plurality force-sensing elements including a sensing rod positioned along the first member or the second member of the needle driver, the sensing rod being in alignment with a direction of elongation of the first member or the second member and the sensing rod being operable for measuring one or more values associated with the tensioning force.

4. The device of claim 3, wherein the sensing rod is positioned within the first member or the second member of the needle driver.

5. The device of claim 1, further comprising a clamp device configured for engagement with the first member or the second member of the needle driver, wherein the plurality of force-sensing elements are positioned along the clamp device.

6. The device of claim 5, the clamp device including a spine having:
a first prong that extends from a first lateral side of the spine to contact the first member or the second member of the needle driver when the clamp device is engaged with the needle driver;
a second prong that extends from a second lateral side and along a midsection of the spine to contact the first member or the second member of the needle driver when the clamp device is engaged with the needle driver; and
a third prong that extends from the first lateral side at a second free end of the spine to contact the first member or the second member of the needle driver when the clamp device is engaged with the needle driver.

7. The device of claim 1, further comprising:
a computing device in communication with the plurality of force-sensing elements and a display device, the computing device including a processor in communication with a memory, the memory including instructions executable by the processor to:
access, at the processor, respective output values measured at the first force-sensing element, the second force-sensing element, and the third force-sensing element;
determine a first value based on a difference between respective output values of the second force-sensing element and the third force-sensing element, the first value corresponding to a first lateral force component directed perpendicular to a longitudinal axis collectively defined by the first member and the second member;
determine a second value based on a difference between respective output values of the second force-sensing element and the first force-sensing element, the second value corresponding to a second lateral force component directed opposite the first lateral force component;
determine, based on the first value and the second value, a value of a tensioning force applied to the tensioning element captured between the first member and the second member; and
display, at the display device in communication with the processor, the value of the tensioning force.

8. A device, comprising:
a tensionometer assembly in operative association with a needle driver, the tensionometer assembly including:

a plurality of force-sensing elements, each of the plurality of force-sending elements being positionable along a first member of the needle driver and including:

a first force-sensing element positioned at a first longitudinal location along the first member distal of a connection between the first member and a second member of the needle driver;

a second force-sensing element positioned at a second longitudinal location along the first member coincident with the connection; and a third force-sensing element positioned at a third longitudinal location along the first member proximal of the connection;

the plurality of force-sensing elements collectively measuring a lateral force component acting on the first member perpendicular to a longitudinal axis collectively defined by the first member and the second member, wherein the second force-sensing element serves as a reference between the first force-sensing element and the third force-sensing element.

9. The device of claim 8, further comprising:

a computing device in communication with the plurality of force-sensing elements and a display device, the computing device including a processor in communication with a memory, the memory including instructions executable by the processor to:

access, at the processor, respective output values measured at the first force-sensing element, the second force-sensing element, and the third force-sensing element;

determine a first value based on a difference between respective output values of the second force-sensing element and the third force-sensing element, the first value corresponding to a first lateral force component directed perpendicular to a longitudinal axis collectively defined by the first member and the second member of the needle driver;

determine a second value based on a difference between respective output values of the second force-sensing element and the first force-sensing element, the second value corresponding to a second lateral force component directed opposite the first lateral force component;

determine, based on the first value and the second value, a value of a tensioning force applied to a tensioning element captured between the first member and the second member of the needle driver; and display, at the display device in communication with the processor, the value of the tensioning force.

10. The device of claim 8, the plurality of force-sensing elements including a plurality of transducers positionable along the first member or the second member of the needle driver.

11. The device of claim 8, the plurality force-sensing elements including a sensing rod positioned along a first member or a second member of the needle driver, the sensing rod being in alignment with a direction of elongation of the first member or the second member and the sensing rod being operable for measuring one or more values associated with the tensioning force.

12. The device of claim 8, further comprising a clamp device configured for engagement with a first member or a second member of the needle driver, wherein the plurality force-sensing elements are positioned along the clamp device.

13. The device of claim 12, the clamp device including:

a spine configured for engagement along the first member or the second member of the needle driver;

a first prong that extends from a first lateral side of the spine to contact the first member or the second member of the needle driver when the clamp device is engaged with the needle driver;

a second prong that extends from a second lateral side and along a midsection of the spine to contact the first member or the second member of the needle driver when the clamp device is engaged with the needle driver; and a third prong that extends from the first lateral side at a second free end of the spine to contact the first member or the second member of the needle driver when the clamp device is engaged with the needle driver.

* * * * *